US012630860B2

(12) United States Patent
Peace et al.

(10) Patent No.: US 12,630,860 B2
(45) Date of Patent: May 19, 2026

(54) NUCLEIC ACID SEQUENCING

(71) Applicant: Illumina, Inc., San Diego, CA (US)

(72) Inventors: Jared Peace, San Diego, CA (US); Jeanine Montano, San Diego, CA (US); Michael Niziolek, San Diego, CA (US); Ark Silbergleit, San Diego, CA (US); Petr Capek, San Diego, CA (US); Peter McInerney, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 1192 days.

(21) Appl. No.: 17/618,811

(22) PCT Filed: Mar. 9, 2021

(86) PCT No.: PCT/EP2021/055922
§ 371 (c)(1),
(2) Date: Dec. 13, 2021

(87) PCT Pub. No.: WO2021/180724
PCT Pub. Date: Sep. 16, 2021

(65) Prior Publication Data
US 2022/0251626 A1     Aug. 11, 2022

Related U.S. Application Data

(60) Provisional application No. 62/987,047, filed on Mar. 9, 2020.

(51) Int. Cl.
*C12Q 1/6806*     (2018.01)
*C12Q 1/6837*     (2018.01)
*C12Q 1/6869*     (2018.01)

(52) U.S. Cl.
CPC ......... *C12Q 1/6806* (2013.01); *C12Q 1/6837* (2013.01); *C12Q 1/6869* (2013.01)

(58) Field of Classification Search
None
See application file for complete search history.

(56) References Cited

U.S. PATENT DOCUMENTS

| | | |
|---|---|---|
| 5,302,509 A | 4/1994 | Cheeseman |
| 2012/0316086 A1 | 12/2012 | Lin |

| | | | |
|---|---|---|---|
| 2013/0116153 A1 | 5/2013 | Bowen | |
| 2013/0225421 A1 | 8/2013 | Li | |
| 2015/0211062 A1 | 7/2015 | Ronaghi | |
| 2016/0318016 A1 | 11/2016 | Hou | |
| 2017/0219554 A1* | 8/2017 | Lee ................. | G01N 33/5438 |
| 2018/0037950 A1 | 2/2018 | Gunderson | |

FOREIGN PATENT DOCUMENTS

| | | |
|---|---|---|
| EP | 1910559 | 4/2008 |
| EP | 2 532 754 | 12/2012 |
| EP | 2961524 | 1/2016 |
| JP | 2014-518639 | 8/2014 |
| WO | WO1998/44151 | 10/1998 |
| WO | WO1998/44152 | 10/1998 |
| WO | WO2000/18957 | 4/2000 |
| WO | WO2007/091077 | 8/2007 |
| WO | WO2008/041002 | 4/2008 |
| WO | WO2013/188582 | 12/2013 |
| WO | WO 2015/189621 | 12/2015 |

OTHER PUBLICATIONS

Sambrook et al., 2001, Molecular Cloning, A Laboratory Manual, 3rd Ed, Cold Spring Harbor Laboratory Press, Cold Spring Harbor Laboratory Press, NY; Current Protocols, eds Ausubel et al.
Anonymous, "Optimizing Cluster Density on Illumina Sequencing Systems; Understanding cluster density limitation and strategies for preventing under- and overclustering" Jan. 2016. pp. 1-12. Retrieved from internet: URL:https://emea.illumina.com/content/dam/illumina-marketing/documents/products/other/miseq-overclustering-primer-770-2014-038.pdf.

* cited by examiner

*Primary Examiner* — Christopher M Gross
(74) *Attorney, Agent, or Firm* — Illumina, Inc.

(57)     ABSTRACT

A method of preparing templates for high throughput nucleic acid sequencing, comprising: a) providing a solid support, wherein said solid support comprises a plurality of nucleic acid primers immobilised adaptor nucleic acid sequences which hybridise to one or more of the nucleic acid primers, and the library preparation having a nucleic acid concentration of 400 pM or less; c) allowing single stranded fragments of template nucleic acid to bind to said nucleic acid primers, thereby immobilising said single stranded fragments on said solid support; and d) repeating steps b) and c) at least three further times, i.e. multiple loadings or rounds of template hybridization to improve occupation rates, e.g., of nanowells on a flow cell.

20 Claims, 4 Drawing Sheets

NUCLEIC ACID SEQUENCING

RELATED APPLICATIONS

This application is the U.S. national phase entry of PCT App. No. PCT/EP2021/055922 filed Mar. 9, 2021 which published in English as WO 2021/180724 on Sep. 16, 2021 which claims priority to U.S. Prov. App. No. 62/987,047 filed Mar. 9, 2020 which are each incorporated herein by reference in its entirety.

FIELD

The present invention relates to improvements in methods of high throughput nucleic acid sequencing, and in particular to improvements in methods of preparing templates for high throughput nucleic acid sequencing.

BACKGROUND

Nucleic acid sequencing methods have been known in the art for many years. Some such methods are based on successive cycles of incorporation of fluorescently labeled nucleic acid analogues. In such "sequencing by synthesis" or "cycle sequencing" methods the identity of the added base is determined after each nucleotide addition by detecting the fluorescent label.

In particular, U.S. Pat. No. 5,302,509 describes a method for sequencing a polynucleotide template which involves performing multiple extension reactions using a DNA polymerase or DNA ligase to successively incorporate labeled polynucleotides complementary to a template strand. In such a "sequencing by synthesis" reaction a new polynucleotide strand based-paired to the template strand is built up in the 5' to 3' direction by successive incorporation of individual nucleotides complementary to the template strand. The substrate nucleoside triphosphates used in the sequencing reaction are labeled at the 3' position with different 3' labels, permitting determination of the identity of the incorporated nucleotide as successive nucleotides are added.

In order to maximise the throughput of nucleic acid sequencing reactions it is advantageous to be able to sequence multiple template molecules in parallel. Parallel processing of multiple templates can be achieved with the use of nucleic acid array technology. These arrays typically consist of a high-density matrix of polynucleotides immobilised onto a solid support material.

Various methods for fabrication of arrays of immobilised nucleic assays have been described in the art. Of particular interest, WO 98/44151 and WO 00/18957 both describe methods of nucleic acid amplification which allow amplification products to be immobilised on a solid support in order to form arrays comprised of clusters or "colonies" formed from a plurality of identical immobilised polynucleotide strands and a plurality of identical immobilised complementary strands. The nucleic acid molecules present in DNA colonies on the clustered arrays prepared according to these methods can provide templates for sequencing reactions, for example as described in WO 98/44152.

In current high throughput next generation sequencing (NGS) methods, sequencing chemistry generally takes place within a flow cell, to which nucleic acids and other reagents may be introduced. To prepare the template strands, source nucleic acids are fragmented, and the fragments ligated to adapter sequences. These adapter sequences are designed to hybridise to short primer sequences which are immobilised onto a solid support within a flow cell, with the sequencing templates then being amplified, resulting in clusters of identical template strands which are then sequenced. Ideally, these clusters are of similar size and are spaced apart from other clusters, to achieve accurate resolution when imaging. Further sequencing reactions then take place on the flow cell, with the results being imaged and sequence reads being aligned, to arrive at a final sequence for the template.

In order to maintain physical separation of the different clusters, a flow cell may include patterned nanowells formed (for example) by photolithography; only the nanowells include the immobilised primer sequences, and hence each cluster will form within a nanowell. The nanowell patterning determines a suitable cluster spacing and location. To maintain distinctness of each cluster, it is desirable for a single template strand initially to hybridise within a given nanowell; as such, template DNA is typically introduced to the flow cell in low molar quantities (on the order of 10-20 pM). Further, amplification may be carried out using an exclusion amplification technique, which permits simultaneous seeding of the template strand in the nanowell and amplification, thereby promoting monoclonal clusters.

As NGS methods continue to improve, attempts are being made to increase the density and number of nanowells within a flow cell, to permit even greater throughput of sequencing. However, the present inventors have found that, when using higher density patterned flow cells, low molar concentrations of template DNA may be inefficient to use; for example, leading to lower proportions of occupied nanowells. Low template seeding concentration may lead to elevated duplicate levels and lower usable yield. Further, many commonly used library preparation methods may be unsuitable for modification to obtain increased template nucleic acid concentrations. In order to mitigate low sample concentrations, the present inventors propose modified methods which make use of a flow cell as a nucleic acid capture device to increase the effective usable concentration of low concentration sequencing templates.

SUMMARY

According to an aspect of the invention, there is provided a method of preparing a template for a nucleic acid sequencing reaction, the method comprising:

- a) providing a solid support, wherein said solid support comprises a plurality of nucleic acid primers immobilised thereon;
- b) contacting a nucleic acid library preparation with the solid support, the library preparation comprising a plurality of single stranded fragments of template nucleic acid to be sequenced, the template nucleic acid fragments further comprising one or more adaptor nucleic acid sequences which hybridise to one or more of the nucleic acid primers, and the library preparation having a nucleic acid concentration of 400 pM or less;
- c) allowing single stranded fragments of template nucleic acid to bind to said nucleic acid primers, thereby immobilising said single stranded fragments on said solid support; and
- d) repeating steps b) and c) at least three further times;
- to thereby provide a solid support having single stranded fragments of template nucleic acid immobilised thereon.

According to a further aspect of the invention, there is provided a method of preparing a template for a nucleic acid sequencing reaction, the method comprising:

- a) providing a flow cell comprising a solid support having a plurality of nanowells formed thereon, each nanowell comprising a plurality of nucleic acid primers immobilised on the solid support, and the nanowells being formed in a patterned array having a pitch of 500 nm or less;

b) contacting a nucleic acid library preparation with the flow cell, the library preparation comprising a plurality of single stranded fragments of template nucleic acid to be sequenced, the template nucleic acid fragments further comprising one or more adaptor nucleic acid sequences which hybridise to one or more of the nucleic acid primers, and the library preparation having a nucleic acid concentration of 400 pM or less;

c) allowing single stranded fragments of template nucleic acid to bind to said nucleic acid primers, thereby immobilising said single stranded fragments in the nanowells; and d) repeating steps b) and c) at least three further times;

to thereby provide a flow cell having single stranded fragments of template nucleic acid immobilised in nanowells.

The present inventors have determined that such a method addresses the disadvantages of using low concentration nucleic acid libraries by permitting multiple loading "pushes" of the library. Each such push improves occupation rates of the nanowells. Multiple rounds of template hybridisation and capture at low DNA concentration increase effective DNA concentration bringing them into the necessary range. This can significantly lower library prep concentration requirements and reduce template waste due to system dead volumes and the like.

The method may comprise repeating steps b) and c) at least four, five, six, seven, eight, nine, or more further times. The effective nucleic acid concentration is believed to be given by number of repeats multiplied by original nucleic acid concentration. For example, four repeats of a 200 pM sample gives an effective concentration of 800 pM. In preferred embodiments of the invention, the effective nucleic acid concentration is at least 800 pM, preferably at least 1000 pM.

The library preparation may have a nucleic acid concentration of 350 pM or less, 300 pM or less, 250 pM or less, or 200 pM or less. The library preparation may have a nucleic acid concentration of at least 50 pM, at least 100 pM, or at least 150 pM.

Repetition of the contacting step may take place with the same library preparation, or with a different library preparation. For example, the method may comprise washing unbound fragments of template nucleic acid from the flow cell, and recovering and reintroducing the unbound fragments to the flow cell. In preferred embodiments, however, the repeated contacting steps make use of a fresh sample drawn from the same initial library preparation.

The method may comprise denaturing a library preparation comprising double stranded fragments of template nucleic acid to be sequenced, to obtain the single stranded fragments of template nucleic acid to be sequenced. The denaturing step may be carried out on the flow cell; for example, the double stranded fragment library may be introduced to the flow cell, followed by denaturation, to result in a single stranded fragment library contacting the flow cell. In preferred embodiments, denaturation may be carried out prior to contacting the flow cell.

The method may further comprise amplifying the immobilised single stranded fragments of nucleic acid, to thereby generate multiple copies of the fragments. In preferred embodiments, amplification takes place using exclusion amplification; for example, as described in WO 2013/188582.

In preferred embodiments of the invention, the solid support is glass, and includes a patterned nanowell array thereon. The nanowell array may be formed by photolithography. The pitch of the nanowell array (that is, the centre-to-centre distance between nanowells) is preferably less than 750 nm, more preferably less than 500 nm, more preferably less than 400 nm, and most preferably 350 nm or less. The flow cell may comprise multiple lanes formed on the solid support, with each lane including a portion of the patterned nanowell array. For example, the flow cell may be of the type produced by Illumina, Inc, of San Diego, USA, for use with the NovaSeq 6000 system. Illustrative methods of producing certain types of solid support having a patterned nanowell array thereon, and flow cells comprising such solid supports are set out in EP 2 961 524.

The method may further comprise sequencing the immobilised single stranded fragments of nucleic acid.

DETAILED DESCRIPTION

In its various aspects the invention generally relates to improvements in methods of high throughput nucleic acid sequencing, and in particular to improvements in methods of preparing templates for high throughput nucleic acid sequencing.

When referring to attachment of molecules (e.g. nucleic acids) to a solid support, the terms "immobilised" and "attached" are used interchangeably herein and both terms are intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilised or attached to the support under the conditions in which it is intended to use the support, for example in applications requiring nucleic acid amplification and/or sequencing. When referring to attachment of nucleic acids to other nucleic acids, then the terms "immobilised" and "hybridised" are used herein, and generally refer to hydrogen bonding between complementary nucleic acids.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fibre bundles, and polymers. A particularly useful material is glass. Other suitable substrate materials may include polymeric materials, plastics, silicon, quartz (fused silica), boro float glass, silica, silica-based materials, carbon, metals, an optical fibre or optical fibre bundles, sapphire, or plastic materials such as COCs and epoxies. The particular material can be selected based on properties desired for a particular use. For example, materials that are transparent to a desired wavelength of radiation are useful for analytical techniques that will utilize radiation of the desired wavelength, such as one or more of the techniques set forth herein. Conversely, it may be desirable to select a material that does not pass radiation of a certain wavelength (e.g. being opaque, absorptive or reflective). This can be useful for formation of a mask to be used during manufacture of the structured substrate; or to be used for a chemical reaction or analytical detection carried out using the structured substrate. Other properties of a material that can be exploited are inertness or reactivity to certain reagents used in a downstream process; or ease of manipulation or low cost during a manufacturing process manufacture. Further examples of materials that can be used in the structured substrates or methods of the present disclosure are described in U.S. Ser. No. 13/661,524 and US Pat. App. Pub. No. 2012/0316086 AI, each of which is incorporated herein by reference.

Certain embodiments of the invention make use of solid supports comprised of a substrate or matrix (e.g. glass slides, polymer beads etc.) which has been "functionalised", for example by application of a layer or coating of an intermediate material comprising reactive groups which permit covalent attachment to biomolecules, such as polynucleotides. Examples of such supports include, but are not limited to, a substrate such as glass. In such embodiments, the biomolecules (e.g. polynucleotides) may be directly covalently attached to the intermediate material but the intermediate material may itself be non-covalently attached to the substrate or matrix (e.g. the glass substrate). The term "covalent attachment to a solid support" is to be interpreted accordingly as encompassing this type of arrangement. Alternatively, the substrate such as glass may be treated to permit direct covalent attachment of a biomolecule; for example, glass may be treated with hydrochloric acid, thus exposing the hydroxyl groups of the glass, and phosphite-triester chemistry used to directly attach a nucleotide to the glass via a covalent bond between the hydroxyl group of the glass and the phosphate group of the nucleotide.

In aspects of the invention, covalent attachment can be achieved through a sulphur-containing nucleophile, such as phosphorothioate, present at the 5' end of a polynucleotide strand.

As used herein, the term "nanowell" refers to a discrete concave feature in a solid support having a surface opening that is completely surrounded by interstitial region(s) of the surface. Wells can have any of a variety of shapes at their opening in a surface including but not limited to round, elliptical, square, polygonal, star shaped (with any number of vertices) etc. The cross section of a well taken orthogonally with the surface can be curved, square, polygonal, hyperbolic, conical, angular, etc. In preferred embodiments of the invention, a nanowell array comprises multiple nanowells set out on a solid support; a patterned nanowell array comprises a repeating arrangement of nanowells such that the relative arrangement of nanowells at one part of the solid support is the same as the relative arrangement of nanowells at at least one other part of the solid support. The pitch of a nanowell array is the centre-to centre distance between two adjacent nanowells.

As will be understood by the skilled person, a double-stranded nucleic acid will typically be formed from two complementary polynucleotide strands comprised of deoxyribonucleotides joined by phosphodiester bonds, but may additionally include one or more ribonucleotides and/or non-nucleotide chemical moieties and/or non-naturally occurring nucleotides and/or non-naturally occurring backbone linkages. In particular, the double-stranded nucleic acid may include non-nucleotide chemical moieties, e.g. linkers or spacers, at the 5' end of one or both strands. By way of non-limiting example, the double-stranded nucleic acid may include methylated nucleotides, uracil bases, phosphorothioate groups, also peptide conjugates etc. Such non-DNA or non-natural modifications may be included in order to confer some desirable property to the nucleic acid, for example to enable covalent attachment to a solid support, or to act as spacers to position the site of cleavage an optimal distance from the solid support. A single stranded nucleic acid consists of one such polynucleotide strand. Where a polynucleotide strand is only partially hybridised to a complementary strand—for example, a long polynucleotide strand hybridised to a short nucleotide primer—it may still be referred to herein as a single stranded nucleic acid.

A template nucleic acid to be sequenced will comprise a "target" region that it is desired to fully or partially sequence. The nature of the target region is not limiting to the invention. It may be of previously known or unknown sequence and may be derived, for example, from a genomic DNA fragment, a cDNA, etc. The template nucleic acid molecule also includes non-target sequences, for example at the 5' and 3' ends of one or both strands (if double stranded), flanking the target region. If the template nucleic acid is formed by solid-phase nucleic acid amplification, these non-target sequences may be derived from the primers used for the amplification reaction. Alternatively, the non-target sequences may be ligated to fragmented target sequences to incorporate them into the nucleic acid molecule.

In embodiments of the invention, a double stranded nucleic acid may be subjected to denaturing conditions in order to provide single stranded nucleic acids. Suitable denaturing conditions will be apparent to the skilled reader with reference to standard molecular biology protocols (Sambrook et al., 2001, Molecular Cloning, A Laboratory Manual, 3rd Ed, Cold Spring Harbor Laboratory Press, Cold Spring Harbor Laboratory Press, NY; Current Protocols, eds Ausubel et al).

Denaturation (and subsequent re-annealing of the cleaved strands) results in the production of a sequencing template which is partially or substantially single-stranded. A sequencing reaction may then be initiated by hybridisation of a sequencing primer to the single-stranded portion of the template. In embodiments of the invention, sequencing can be carried out using a strand-displacement polymerase enzyme.

In embodiments of the invention, the term "solid support" as used herein refers to the material to which the polynucleotide molecules are attached. Suitable solid supports are available commercially, and will be apparent to the skilled person. The supports can be manufactured from materials such as glass, ceramics, silica and silicon. Supports with a gold surface may also be used. The supports usually comprise a flat (planar) surface, or at least a structure in which the polynucleotides to be interrogated are in approximately the same plane. Any suitable size support may be used. Alternatively, the solid support can be non-planar, e.g., a microbead.

In embodiments of the invention, the methods of the invention may be used to prepare templates for nucleic acid sequencing. The immobilised single stranded nucleic acids can be amplified to provide clustered arrays of nucleic acid colonies generated by solid-phase nucleic acid amplification. In this context, the term "solid-phase amplification" refers to an amplification reaction which is analogous to standard PCR, except that the forward and/or reverse amplification primers are immobilised (e.g. covalently attached) to a solid support at or near the 5' end. The products of the PCR reaction are thus extended strands derived by extension of the amplification primers that are immobilised on the solid support at or near the 5' end. Solid-phase amplification may itself be carried out, for example, using procedures analogous to those described in WO 98/44151 and WO 00/18957.

As a first step in colony generation by solid-phase amplification a mixture of forward and reverse amplification primers may be immobilised or "grafted" onto the surface of a suitable solid support. The grafting step will generally involve covalent attachment of the primers to the support at or near the 5' end, leaving the 3' end free for primer extension.

The amplification primers are typically oligonucleotide molecules having the following structures:

Forward primer: A-L-S1
Reverse primer: A-L-S2

Wherein A represents an optional moiety which allows attachment to a solid support, L represents an optional linker moiety and S1 and S2 are polynucleotide sequences which permit amplification of a substrate nucleic acid molecule comprising a target region that it is desired to (fully or partially) sequence.

The mixture of primers grafted onto the solid support will generally comprise substantially equal amounts of the forward and reverse primers.

Group A can be any moiety (including a non-nucleotide chemical modification) which enables attachment (preferably covalent) to a solid support. In aspects of the invention group A may comprise a sulphur-containing nucleophile, such as phosphorothioate, present at the 5' end of a polynucleotide strand. Alternatively, group A may be omitted where suitable chemistry is used to directly attach either the linker or the nucleic acid directly to the solid support.

L represents a linker or spacer which may be included but is not strictly necessary. The linker may be included in order to ensure that a cleavage site present in the immobilised polynucleotide molecules generated as a result of the amplification reaction is positioned at an optimum distance from the solid support, or the linker may itself contain a cleavage site.

The linker may be a carbon-containing chain with a formula $(CH_2)_n$ wherein "n" is from 1 to about 1500, for example less than about 1000, preferably less than 100, e.g. from 2-50, particularly 5-25. However, a variety of other linkers may be employed with the only restriction placed on their structures being that the linkers are stable under conditions under which the polynucleotides are intended to be used subsequently, e.g. conditions used in DNA amplification and sequencing.

Linkers which do not consist of only carbon atoms may also be used. Such linkers may include polyethylene glycol (PEG)

Linkers formed primarily from chains of carbon atoms and from PEG may be modified so as to contain functional groups which interrupt the chains. Examples of such groups include ketones, esters, amines, amides, ethers, thioethers, sulfoxides, sulfones. Separately or in combination with the presence of such functional groups may be employed alkene, alkyne, aromatic or heteroaromatic moieties, or cyclic aliphatic moieties (e.g. cyclohexyl). Cyclohexyl or phenyl rings may, for example, be connected to a PEG or $(CH_2)_n$ chain through their 1- and 4-positions.

As an alternative to the linkers described above, which are primarily based on linear chains of saturated carbon atoms, optionally interrupted with unsaturated carbon atoms or heteroatoms, other linkers may be envisaged which are based on nucleic acids or monosaccharide units (e.g. dextrose). It is also within the scope of this invention to utilise peptides as linkers.

In a further embodiment the linker may comprise one or more nucleotides. Such nucleotides may also be referred to herein as "spacer" nucleotides. Typically, from 1 to 20, more preferably from 1 to 15 or from 1 to 10, and more particularly 2, 3, 4, 5, 6, 7, 8, 9 or 10 spacer nucleotides may be included. Most preferably the primer will include 10 spacer nucleotides. It is preferred to use polyT spacers, although other nucleotides and combinations thereof can be used. In one preferred embodiment the primer may include 10T spacer nucleotides.

For the primer grafting reaction to proceed a mixture of the amplification primers is applied to a solid support under conditions which permit reaction between moiety A (if present) and the support, or between the nucleic acid and the support. The solid support may be suitably functionalised to permit covalent attachment via moiety A. The result of the grafting reaction is a substantially even distribution of the primers over at least a portion of the solid support. Where the solid support includes nanowells, then in preferred embodiments primers are restricted to the location of the nanowells, and are not present in interstitial regions of the solid support.

The nucleic acid library preparation is typically contacted with the flow cell in free solution. The amplification reaction may then proceed substantially as described in WO 98/44151. Briefly, following attachment of the primers the solid support is contacted with the template to be amplified under conditions which permit hybridisation between the template and the immobilised primers. The template is usually added in free solution under suitable hybridisation conditions, which will be apparent to the skilled reader. Typically, hybridisation conditions are, for example, 5×SSC at 40° C. Solid-phase amplification can then proceed, the first step of the amplification being a primer extension step in which nucleotides are added to the 3' end of the immobilised primer hybridised to the template to produce a fully extended complementary strand. This complementary strand will thus include at its 3' end a sequence which is capable of binding to the second primer molecule immobilised on the solid support. Further rounds of amplification (analogous to a standard PCR reaction) lead to the formation of clusters or colonies of template molecules bound to the solid support. Other amplification procedures may be used, and will be known to the skilled person. For example, amplification may be isothermal amplification using a strand displacement polymerase; or may be exclusion amplification as described in WO 2013/188582.

Sequences S1 and S2 in the amplification primers may be specific for a particular target nucleic acid that it is desired to amplify, but in other embodiments sequences S1 and S2 may be "universal" primer sequences which enable amplification of any target nucleic acid of known or unknown sequence which has been modified to enable amplification with the universal primers.

Suitable nucleic acids to be amplified with universal primers may be prepared by modifying polynucleotides comprising the target region to be amplified (and sequenced) by addition of known adaptor sequences to the 5' and 3' ends of the target polynucleotides to be amplified. The target molecules themselves may be any polynucleotide molecules it is desired to sequence (e.g. random fragments of human genomic DNA). The adaptor sequences enable amplification of these molecules on a solid support to form clusters using forward and reverse primers having the general structure described above, wherein sequences S1 and S2 are universal primer sequences.

The adaptors are typically short oligonucleotides that may be synthesised by conventional means. The adaptors may be attached to the 5' and 3' ends of target nucleic acid fragments by a variety of means (e.g. subcloning, ligation, etc.). More specifically, two different adaptor sequences are attached to a target nucleic acid molecule to be amplified such that one adaptor is attached at one end of the target nucleic acid molecule and another adaptor is attached at the other end of the target nucleic acid molecule. The resultant construct comprising a target nucleic acid sequence flanked by adaptors may be referred to herein as a "substrate nucleic acid construct". The target polynucleotides may advantageously be size-fractionated prior to modification with the adaptor sequences.

The adaptors contain sequences which permit nucleic acid amplification using the amplification primer molecules immobilised on the solid support. These sequences in the adaptors may be referred to herein as "primer binding sequences". In order to act as a template for nucleic acid amplification, a single strand of the template construct must contain a sequence which is complementary to sequence S1 in the forward amplification primers (such that the forward primer molecule can bind and prime synthesis of a complementary strand) and a sequence which corresponds to sequence S2 in the reverse amplification primer molecules (such that the reverse primer molecule can bind to the complementary strand). The sequences in the adaptors which permit hybridisation to primer molecules will typically be around 20-40 nucleotides in length, although the invention is not limited to sequences of this length.

The precise identity of sequences S1 and S2 in the amplification primers, and hence the cognate sequences in the adaptors, are generally not material to the invention, as long as the primer molecules are able to interact with the amplification sequences in order to direct PCR amplification. The criteria for design of PCR primers are generally well known to those of ordinary skill in the art.

Solid-phase amplification by either the method analogous to that of WO 98/44151 or that of WO 00/18957 will result in production of a clustered array comprised of colonies of "bridged" amplification products. Both strands of the amplification products will be immobilised on the solid support at or near the 5' end, this attachment being derived from the original attachment of the amplification primers. Typically, the amplification products within each colony will be derived from amplification of a single template (target) molecule.

Modifications required to enable subsequent cleavage of the bridged amplification products may be advantageously included in one or both amplification primers. Such modifications may be placed anywhere in the amplification primer, provided this does not affect the efficiency of the amplification reaction to a material extent. Thus, the modifications which enable cleavage may form part of the linker region L or one or both of sequences S1 or S2. By way of example, the amplification primers may be modified to include inter alia diol linkages, uracil nucleotides, ribonucleotides, methylated nucleotides, peptide linkers, PCR stoppers or recognition sequences for a restriction endonuclease.

Because all nucleic acid molecules prepared by solid-phase amplification will ultimately contain sequences derived from the amplification primers, any modifications in the primers will be carried over into the amplified products.

Alternative amplification methods (for example, isothermal amplification; or exclusion amplification as described in WO 2013/188582) may be used.

The invention may also include a sequencing step; or aspects of the invention may also encompass methods of sequencing nucleic acid templates generated using the methods of the invention. Thus, the invention provides a method of nucleic acid sequencing comprising providing a template for nucleic acid sequencing using a method as described herein and performing a nucleic acid sequencing reaction to determine the sequence one at least one region of the template.

Sequencing can be carried out using any suitable "sequencing-by-synthesis" technique, wherein nucleotides are added successively to a free 3' hydroxyl group, resulting in synthesis of a polynucleotide chain in the 5' to 3' direction. The nature of the nucleotide added is preferably determined after each addition.

An initiation point for a sequencing reaction may be provided by annealing of a sequencing primer to a single-stranded region of the template. Thus, the invention encompasses methods wherein the nucleic acid sequencing reaction comprises hybridising a sequencing primer to a single-stranded fragment of template nucleic acid immobilised in a nanowell provided in the above aspect of the invention, sequentially incorporating one or more nucleotides into a polynucleotide strand complementary to the region of the template to be sequenced, identifying the base present in one or more of the incorporated nucleotide(s) and thereby determining the sequence of a region of the template.

A preferred sequencing method which can be used in the invention relies on the use of modified nucleotides containing 3' blocking groups that can act as chain terminators. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

The modified nucleotides may carry a label to facilitate their detection. Preferably this is a fluorescent label. Each nucleotide type may carry a different fluorescent label. However, the detectable label need not be a fluorescent label. Any label can be used which allows the detection of an incorporated nucleotide.

One method for detecting fluorescently labeled nucleotides comprises using laser light of a wavelength specific for the labeled nucleotides, or the use of other suitable sources of illumination. The fluorescence from the label on the nucleotide may be detected by a CCD camera or other suitable detection means.

The methods of the invention are not limited to use of the sequencing method outlined above but can be used in conjunction with essentially any sequencing methodology which relies on successive incorporation of nucleotides into a polynucleotide chain. Suitable techniques include, for example, Pyrosequencing™, FISSEQ (fluorescent in situ sequencing), MPSS (massively parallel signature sequencing) and sequencing by ligation-based methods.

The target polynucleotide to be sequenced using the method of the invention may be any polynucleotide that it is desired to sequence. The target polynucleotide may be of known, unknown or partially known sequence, for example in re-sequencing applications. Using the template preparation method described in detail herein it is possible to prepare templates starting from essentially any double-stranded target polynucleotide of known, unknown or partially known sequence. With the use of arrays, it is possible to sequence multiple targets of the same or different sequence in parallel. A particularly preferred application of the method is in the sequencing of fragments of genomic DNA.

These and other aspects of the invention will now be described with reference to the accompanying Figures, in which.

Figure 4:
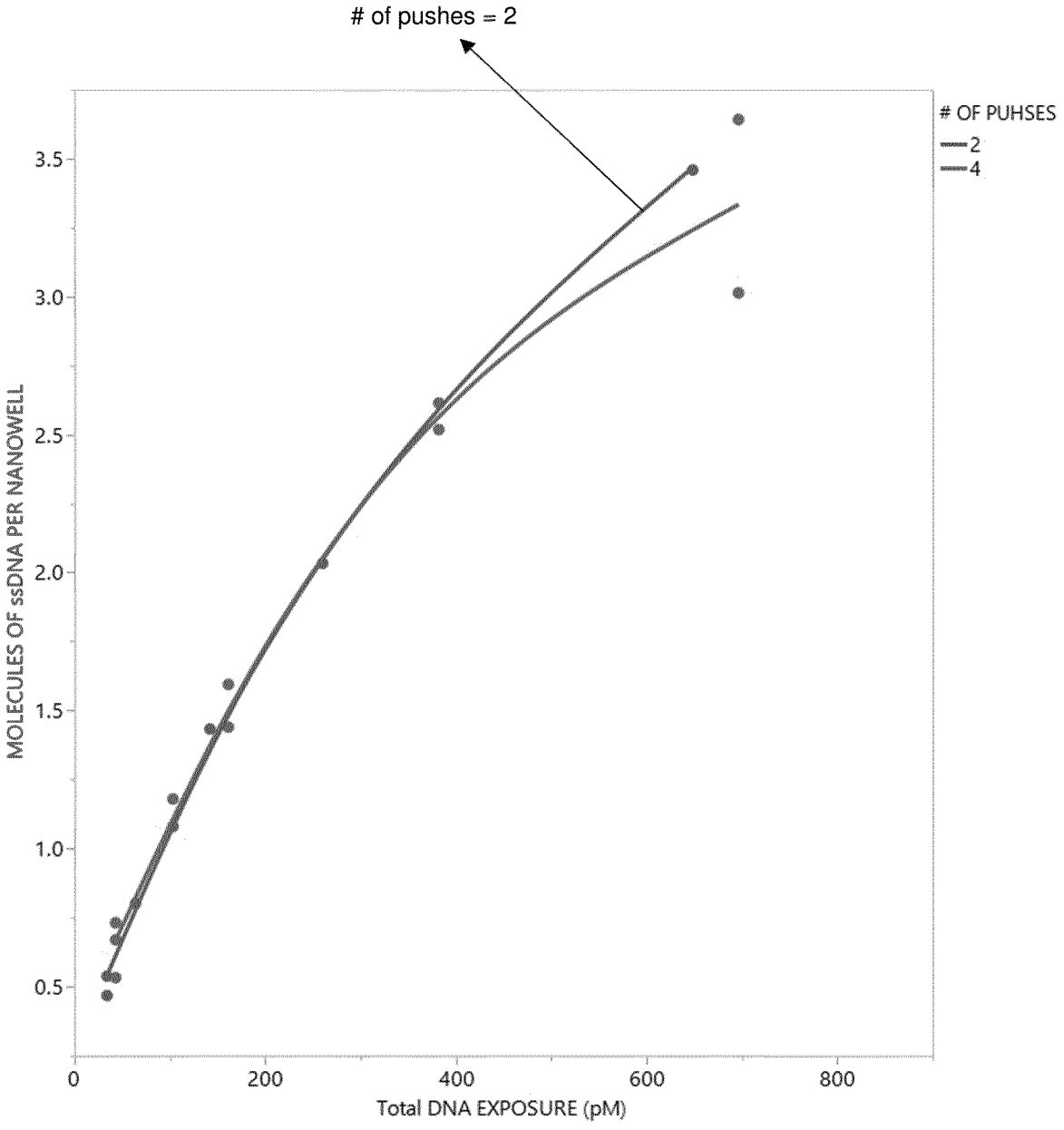

FIG. 4 compares library seeding efficiency with two different multi hybridization workflows.

Figure 5:
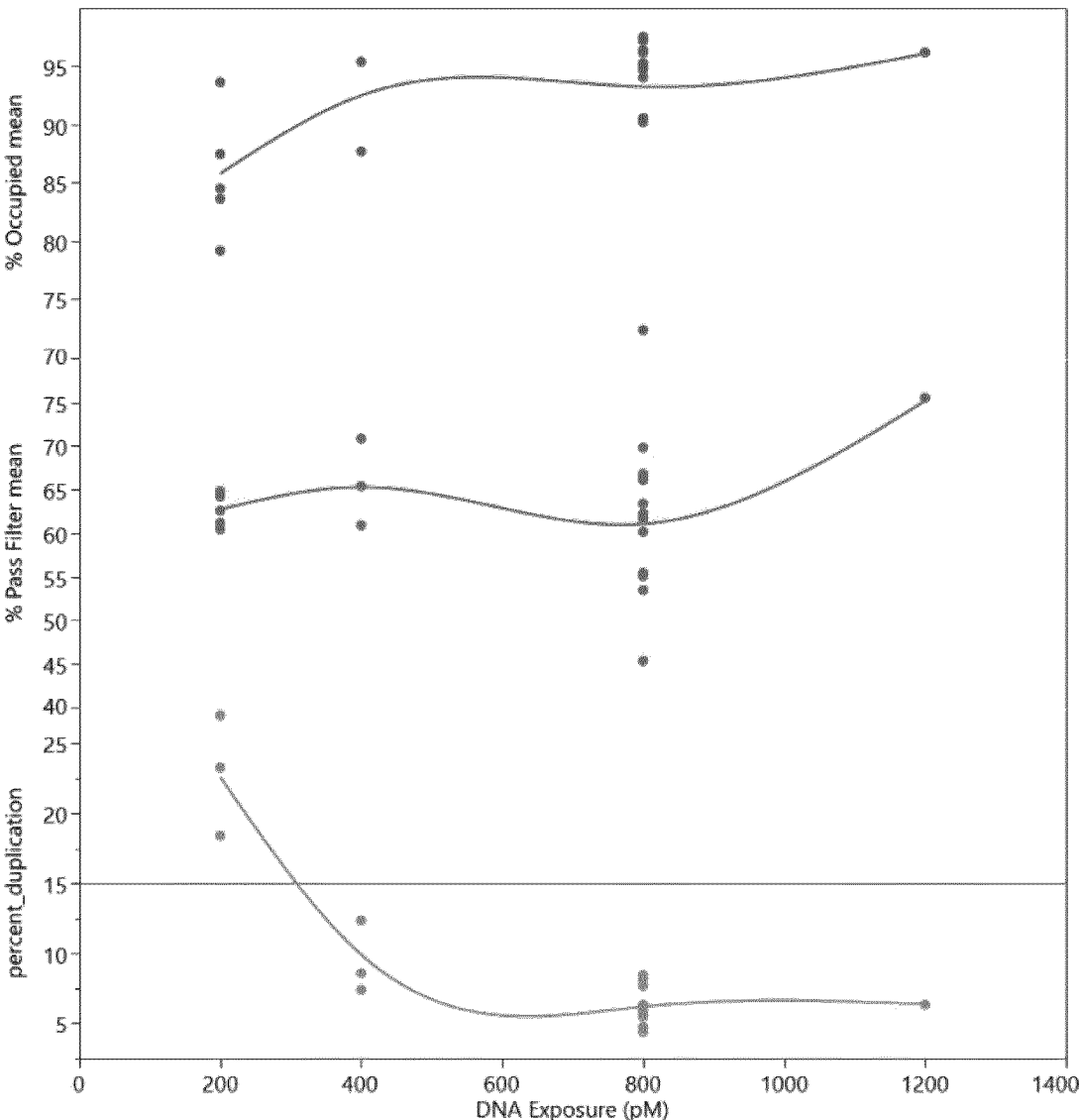

FIG. 5 gives results from a 4-push workflow using a 200 pM library concentration.

Figure 1:
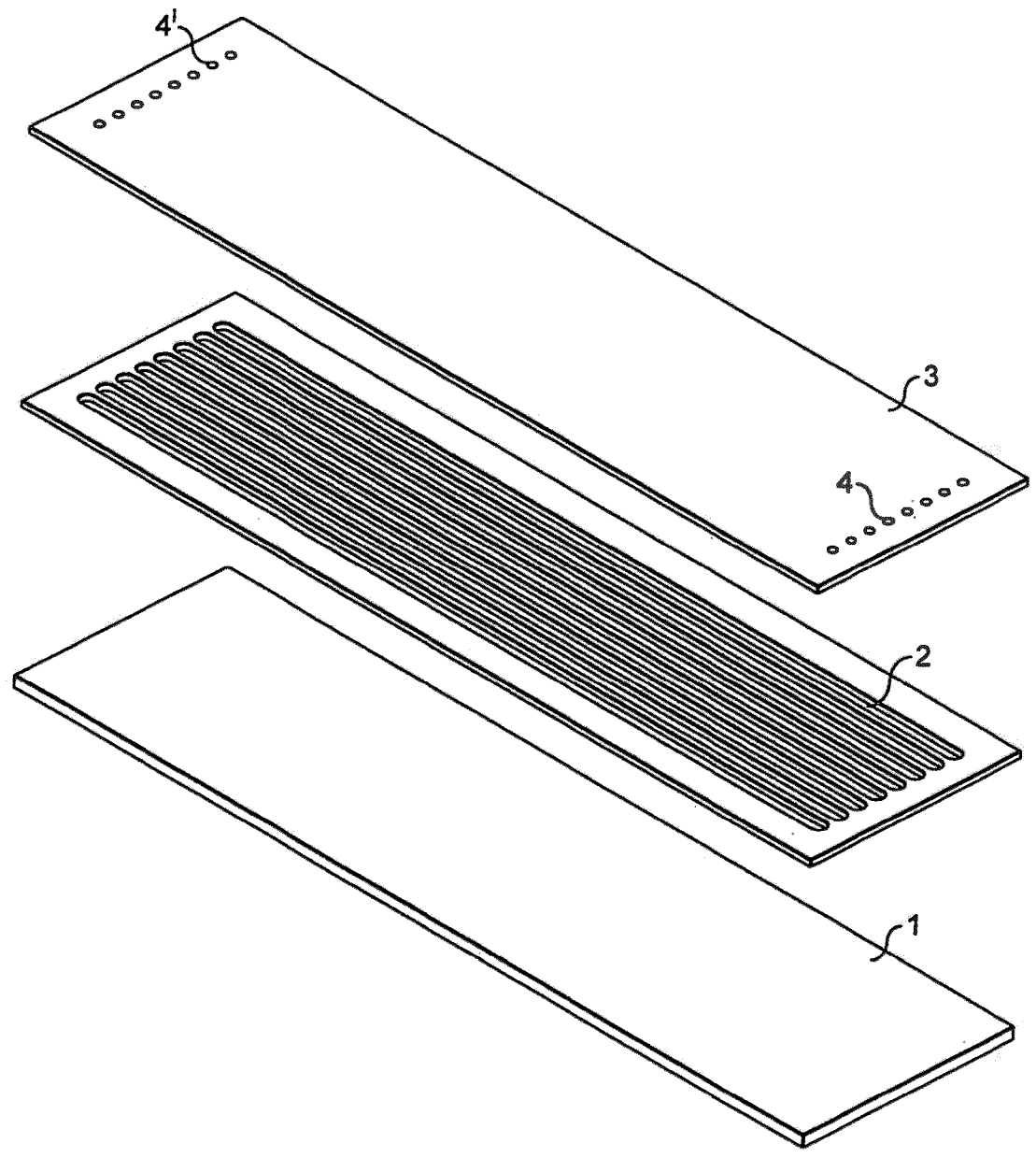
FIG. 1 shows a schematic representation of an illustrative flow cell which may be used with certain methods described herein.

Referring to FIG. 1, this shows a schematic representation of an illustrative flow cell which may be used with certain methods described herein. The flow cell is formed in three layers. The bottom layer 1 is formed of borosilicate glass at a depth of 1000 µm. An etched silicon channel layer (100 µm depth) is placed on top to define 8 separate reaction channels. Top layer 3 (300 µm depth) includes two separate series of 8 holes 4 and 4' in register with the channels of the etched silicon channel layer in order to provide fluid communication with the contents of the channels when the flow cell is assembled in use. The borosilicate glass of the bottom layer 1 is etched with nanowells set out in a patterned array having a 350 nm pitch, and arranged in line with the reaction channels. The interstitial regions—that is, between the channels—are not etched, and do not include nanowells. In use, primers for nucleic acid fragment template capture are bound to the nanowells.

To load the flow cell with a prepared library for sequencing, the following protocols may be used. An initial library of double stranded DNA including appropriate adapters for the sequencing technique to be used may be prepared in any suitable manner known in the art. For example, library preparation kits may be purchased from Illumina, Inc (San Diego, USA) to prepare suitable libraries. The examples described herein were prepared using a TruSeq Human Nano 450 preparation kit.

The below workflow models a 4 push multi hybridization recipe. The total number of hybridization events can be varied up or down depending on the necessary use case and the desired final effective concentration.

Library Denaturation and Dilution:
1. 20 ul of double stranded DNA library is diluted to the appropriate concentration with H₂O or RSB Buffer (available in the TruSeq Human Nano 450 preparation kit). In order to take advantage of the multi hybridization workflow, this working concentration is 4 times lower than the concentration necessary for a standard single event hybridization protocol.
2. Mix the library 1:1 with LDR denaturation reagent (100% formamide).
3. Heat to 65° C. and incubate for 8 minutes to denature the double stranded DNA template.
4. Add 160 ul of HT1 (5×SSC+0.1% Tween20) to dilute the denatured library to the final intended working concentration.
5. Proceed to Template Hybridization Template Hybridization with Multi Hybridization workflow, using an Illumina NovaSeq6000 system:
1. Prime/wet the cartridge lines and flow cell with BB6 buffer.
2. Heat the flow cell to 40° C.
3. Pump denatured and diluted template to the flow cell with an initial flush factor large enough to fully cover the flow cell without dilution from the upstream BB6 buffer.
4. Incubate for 5 minutes.
5. After incubating, pull an additional flow cell volume of denatured and diluted template to the flow cell and incubate for 5 minutes.
6. Repeat step 5 two additional times for a total of 4 total hybridization events.
7. Proceed to cluster generation.

Figure 2:
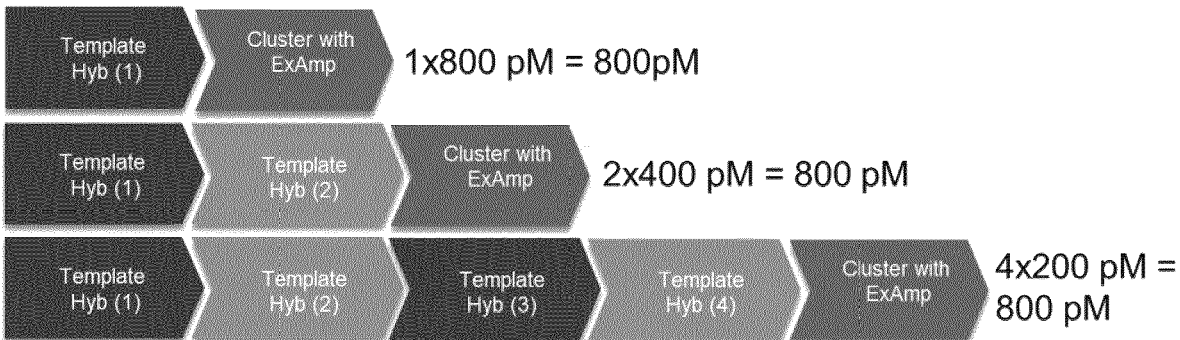
FIG. 2 illustrates the concept of the multi hybridisation workflow.

FIG. 2 illustrates the concept of the multi hybridisation workflow. A typical single push workflow is shown in the top line, where template hybridization takes place once, followed by cluster generation. If the template is loaded at 800 pM concentration, the effective concentration remains 800 pM. The second and third lines set out alternate ways to achieve the same concentration; using two hybridization cycles of 400 pM (second line), or four hybridization cycles at 200 pM (third line). It can be seen that multiple rounds of template hybridization/capture at low DNA concentration increase effective DNA concentration bringing them into the necessary range. This in turn significantly lowers library prep concentration requirements and reduces template waste due to system dead volumes, fluidic lines, etc, and will potentially enable run requeues of low yield library preparations.

Using the above methodology, an initial 2 nM library was prepared and diluted to 200 pM concentration.

|  | Volume (ul) | Concentration (nM) |
| --- | --- | --- |
| Library | 20 | 2 |
| LDR | 20 | n.a. |
| HT1 | 160 | n.a. |
| Final | 200 | 0.2 |

Typical library yields for different applications are shown below:

| Applications | Representative LP assay | Library yield (nM) |
| --- | --- | --- |
| Gene Expression, Whole Transcriptome (RNAseq) | TruSeq | ~20 nM |
| Single Cell (Gene expression) | SureCell | 1 nM |
| Somatic Mutations (Amplicon/ enrichment) | AmpliSeq | 2 nM |
|  | TST170 | ~10 nM |

-continued

| Applications | Representative LP assay | Library yield (nM) |
|---|---|---|
| Whole Exome | Titanium | 12 nM |
| Hu-WGS, PCR-free | TruSeq Nextera (Viper) | 2 nM |
| Hu-WGS, PCR | TruSeq Nano Nextera Flex | 10 nM |

Figure 3:
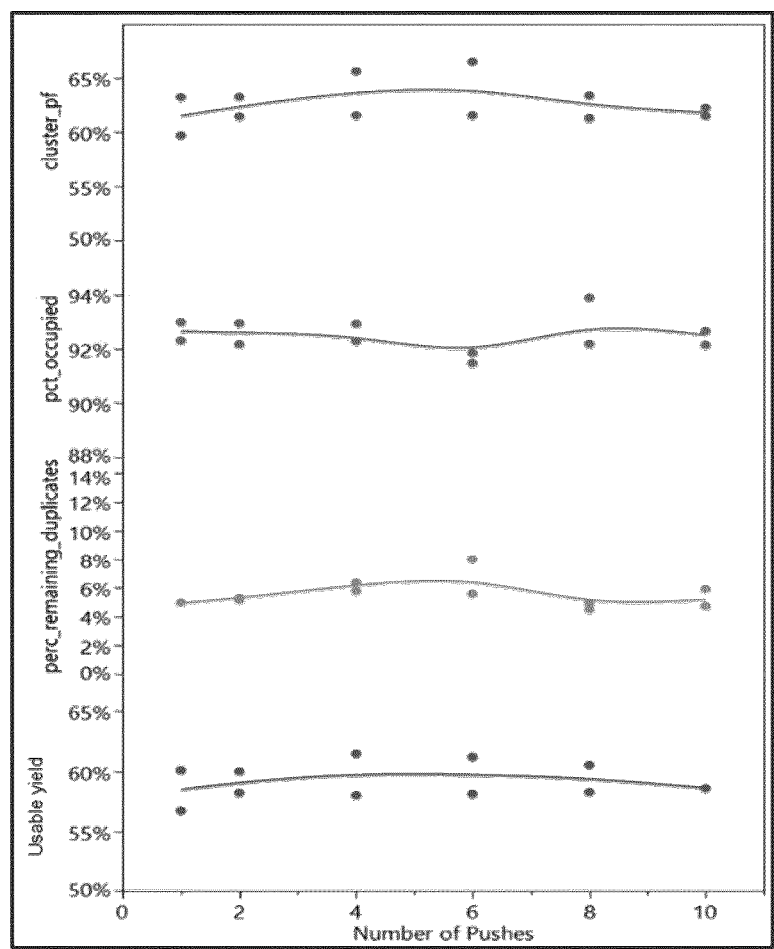
FIG. 3 illustrates results obtained using from 1 to 10 pushes (hybridization cycles) for various metrics.

FIG. 3 illustrates results obtained using from 1 to 10 pushes (hybridization cycles) for various metrics, with each workflow being designed to provide 800 pM effective concentration. The metrics measured included % cluster formation, % occupied nanowells, % remaining duplicates, and % usable yield. It can be seen that, regardless of the number of pushes, the metrics remain within a small band, and multiple pushes up to 10 provide similar metrics as a single push of higher concentration. The optimum for usable yield and cluster formation lies within the 4-6 push range. The flow cell used had a 350 nm nanowell pitch.

FIG. 4 compares library seeding efficiency with two different multi hybridization workflows (2-push vs 4-push). An initial known quantity of library is hybridized to the flow cell in one or multiple rounds, then the template that was hybridized is eluted and qPCR quantified. The initial input and uncaptured template fraction can be quantified with hybridized fraction. The graph shows that 2-push and 4-push provide similar numbers of molecules of ssDNA per nanowell, increasing as total DNA exposure increases up to 700 pM. As long as the final DNA exposure is maintained, total push number can be varied to give similar results. The 2-push protocol utilizes 2× the DNA concentration relative to the 4-push protocol, but maintains similar final molecules per nanowell.

FIG. 5 gives results from a 4-push workflow using a 200 pM library concentration (800 pM effective concentration), on a 350 nm pitch flow cell using the library prepared with a TruSeq Human Nano 450 kit. As total DNA concentration increases to 800 pM, it can be seen that the % occupied nanowells increases, and the % duplication decreases. It can be seen that as concentration increases to 800 pM, % Pass Filter remains consistent showing that the maintaining lower concentrations over multiple pushes results in optimal seeding.

Hence the multiple hybridization workflow appears to be an effective protocol for efficient loading of high density nanowell flow cells without unduly increasing duplicated clusters, and demonstrates that it is possible to use a sequencing flow cell as a DNA capture device in order to increase the effective concentration of a sample to be sequenced, particularly when the sample preparation is of relatively low concentration yield. The preferred four-fold hybridization protocol reduces library input concentration requirements by four times, and potentially enables run requeues of low yield library preps.

The invention claimed is:

1. A method of preparing a template for a nucleic acid sequencing reaction, the method comprising:
   (a) providing a solid support, wherein said solid support comprises a plurality of nucleic acid primers immobilised thereon;
   (b) contacting a nucleic acid library preparation with the solid support, the library preparation comprising a plurality of single stranded fragments of template nucleic acid to be sequenced, the template nucleic acid fragments further comprising one or more adaptor nucleic acid sequences which hybridise to one or more of the nucleic acid primers, and the library preparation having a nucleic acid concentration of 400 pM or less;
   (c) allowing single stranded fragments of template nucleic acid to bind to said nucleic acid primers, thereby immobilising said single stranded fragments on said solid support; and
   (d) repeating steps (b) and (c) three further times, wherein steps (b) to (d) lack an amplification step;
   to thereby provide a solid support having single stranded fragments of template nucleic acid immobilised thereon.

2. The method of claim 1, wherein an effective nucleic acid concentration calculated as number of cycles of step (c) times library nucleic acid concentration is at least 800 pM.

3. The method of claim 1, wherein the library preparation has a nucleic acid concentration of 250 pM or less.

4. The method of claim 1, wherein repetition of the contacting step takes place with the same library preparation as used in step (b).

5. The method of claim 1, comprising denaturing a library preparation comprising double stranded fragments of template nucleic acid to be sequenced, to obtain the single stranded fragments of template nucleic acid to be sequenced used in step (b).

6. The method of claim 1, further comprising amplifying the immobilised single stranded fragments of nucleic acid, to thereby generate multiple copies of the fragments.

7. The method of claim 1, wherein the solid support is glass.

8. The method of claim 1, wherein said solid support is on a flowcell, wherein said solid support has a plurality of nanowells formed thereon, each nanowell comprising a plurality of nucleic acid primers immobilised on the solid support, and the nanowells being formed in a patterned array.

9. The method of claim 8, wherein a pitch of the nanowell array is 500 nm or less.

10. The method of claim 9, wherein the pitch of the nanowell array is 350 nm or less.

11. The method of claim 1, wherein the solid support is a microbead.

12. The method of claim 1, further comprising sequencing the immobilised single stranded fragments of nucleic acid.

13. A method of preparing a template for a nucleic acid sequencing reaction, the method comprising:
   (a) providing a flow cell comprising a solid support having a plurality of nanowells formed thereon, each nanowell comprising a plurality of nucleic acid primers immobilised on the solid support, and the nanowells being formed in a patterned array having a pitch of 500 nm or less;
   (b) contacting a nucleic acid library preparation with the flow cell, the library preparation comprising a plurality of single stranded fragments of template nucleic acid to be sequenced, the template nucleic acid fragments further comprising one or more adaptor nucleic acid sequences which hybridise to one or more of the nucleic acid primers, and the library preparation having a nucleic acid concentration of 400 pM or less;
   (c) allowing single stranded fragments of template nucleic acid to bind to said nucleic acid primers, thereby immobilising said single stranded fragments in the nanowells; and
   (d) repeating steps (b) and (c) three further times, wherein steps (b) to (d) lack an amplification step;

to thereby provide a flow cell having single stranded fragments of template nucleic acid immobilised in nanowells.

14. The method of claim 13, wherein an effective nucleic acid concentration calculated as number of cycles of step (c) times library nucleic acid concentration is at least 800 pM.

15. The method of claim 13, wherein the library preparation has a nucleic acid concentration of 250 pM or less.

16. The method of claim 13, wherein repetition of the contacting step takes place with the same library preparation as used in step (b).

17. The method of claim 13, comprising denaturing a library preparation comprising double stranded fragments of template nucleic acid to be sequenced, to obtain the single stranded fragments of template nucleic acid to be sequenced used in step (b).

18. The method of claim 13, further comprising amplifying the immobilised single stranded fragments of nucleic acid, to thereby generate multiple copies of the fragments.

19. The method of claim 13, wherein the pitch of the nanowell array is 350 nm or less.

20. The method of claim 13, further comprising sequencing the immobilised single stranded fragments of nucleic acid.

\* \* \* \* \*